(12) United States Patent
Dureiko

(10) Patent No.: US 7,283,227 B2
(45) Date of Patent: Oct. 16, 2007

(54) OBLIQUE TRANSMISSION ILLUMINATION INSPECTION SYSTEM AND METHOD FOR INSPECTING A GLASS SHEET

(75) Inventor: Richard D. Dureiko, Corning, NY (US)

(73) Assignee: Corning Incorporated, Corning, NY (US)

( * ) Notice: Subject to any disclaimer, the term of this patent is extended or adjusted under 35 U.S.C. 154(b) by 58 days.

(21) Appl. No.: 11/284,754

(22) Filed: Nov. 21, 2005

(65) Prior Publication Data

US 2007/0115463 A1 May 24, 2007

(51) Int. Cl.
*G01N 21/00* (2006.01)
(52) U.S. Cl. .................. 356/293.1; 356/237.1
(58) Field of Classification Search .......... 356/430, 356/237.1, 239.1, 239.4, 239.7, 239.8, 23; 382/141, 142
See application file for complete search history.

(56) References Cited

U.S. PATENT DOCUMENTS

| | | | | |
|---|---|---|---|---|
| 3,971,621 | A * | 7/1976 | Albrecht-Buehler | 359/390 |
| 4,492,477 | A * | 1/1985 | Leser | 356/430 |
| 4,989,973 | A * | 2/1991 | Noso et al. | 356/239.8 |
| 5,305,139 | A * | 4/1994 | Greenberg | 359/390 |
| 5,570,228 | A * | 10/1996 | Greenberg | 359/389 |
| 6,084,664 | A * | 7/2000 | Matsumoto et al. | 356/237.4 |
| 6,184,977 | B1 * | 2/2001 | Ishida | 356/239.1 |
| 6,256,091 | B1 * | 7/2001 | Kobayashi | 356/237.1 |
| 6,633,377 | B1 * | 10/2003 | Weiss et al. | 356/239.1 |
| 2003/0152276 | A1 * | 8/2003 | Kondo et al. | 382/224 |
| 2005/0206890 | A1 * | 9/2005 | Hurst et al. | 356/239.7 |

OTHER PUBLICATIONS

Abramowitz et al., "Introduction to Oblique Illumination", (2003), pp. 1-13☐☐http://micro.magnet.fsu.edu/primer/techniques/oblique/obliqueintro.html.*
W.S. Jones, "Introduction to Oblique Illumination", Molecular Expressions, Optical Microscopy Primer Specialized Techniques, http://micro.magnet.fsu.edu/primer/techniques/oblique/obliqueintro.html, Aug. 1, 2003.
"Modulation Transfer Function Interactive Java Tutorials: Contrast Enhancement Technique MTF Curves", Molecular Expressions, Optical Microscopy Primer Anatomy of the Microscope, http://microscopy.fsu.edu/primer/java/mtf/contrasttechniques/index.html, 2003.
Galileo Microscopy, "Contrast in Optical Microscopy", Molecular Expressions, Optical Microscopy Primer Specialized Techniques, http://micromagnet.fsu.edu/primer/techniques/contrast.html, Aug. 1, 2004.

* cited by examiner

*Primary Examiner*—Sang H. Nguyen
(74) *Attorney, Agent, or Firm*—Christopher Nicastri, Esq.; William J. Tucker

(57) ABSTRACT

An oblique illumination inspection system and method are described herein that are used to identify a defect (e.g., inclusion, onclusion, scratch, stain, blister, cord or other imperfection associated with a surface discontinuity or material non-homogeneity) on or within a glass sheet (e.g., LCD glass substrate).

10 Claims, 3 Drawing Sheets

OBLIQUE TRANSMISSION ILLUMINATION INSPECTION SYSTEM AND METHOD FOR INSPECTING A GLASS SHEET

BACKGROUND OF THE INVENTION

1. Field of the Invention

The present invention relates to an oblique illumination inspection system and method for identifying defects on or within a glass sheet.

2. Description of Related Art

Manufacturers of glass sheets are always trying to design a new and improved inspection system that can be used to identify defects (e.g., scratches, stains, particle inclusions) that are on or within a glass sheet (e.g., liquid crystal display (LCD) glass substrate). One type of inspection system that is currently being used today relies on a bright field illumination technique to detect, characterize, and classify defects on or within the glass sheet. This type of inspection system is described below with respect to FIG. 1 (PRIOR ART).

Referring to FIG. 1 (PRIOR ART), there is shown a traditional bright field illumination inspection system 100 that is currently used to inspect a glass sheet 102 and identify defects 104 (one shown) on or within the glass sheet 102. The inspection system 100 includes a light source 106 (e.g., fiber line light source 106) and a CCD camera 108. The light source 106 and CCD camera 108 are located on opposite sides of the glass sheet 102, and the light source 106 is located on an optic axis 110 of the CCD camera 108. In operation, the light source 106 emits a light beam 112 which passes through a portion of the glass sheet 102. As shown, the CCD camera 108 and in particular a camera lens 109 receives direct light 112 that passed un-deviated through the transparent defect 104. In addition, the CCD camera 108/camera lens 109 receives light 112a ($D^+$) and 112a ($D^-$) that was diffracted by the transparent defect 104. The camera lens 109 focuses the light 112, 112a ($D^+$) and 112a ($D^-$) onto an image plane 111 within the CCD camera 108. The CCD camera 108 then creates an image which is used to detect, characterize and classify the defect 104.

Although this type of lighting affords a compact design and employs industry standard lighting techniques, the image contrast of certain transparent glass defects, such as silica, scratches, and stains, is relatively poor (see FIG. 5). The poor image contrast hinders the characterization and classification of the transparent defect 104, which adversely impacts the quality of the inspection process. This poor image contrast is primarily due to the interference between the light 112 that passed un-deviated through the transparent defect 104 and the light 112a ($D^+$) and 112a ($D^-$) that was diffracted by the transparent defect 104. In this configuration, light 112a ($D^+$) and 112a ($D^-$) respectively have a positive diffraction order $D^+$ and a negative diffraction order $D^-$ both of which interfere with the un-deviated light 112 to essentially wash out the contrast of the transparent defect 104 in the image. The two problematic diffraction orders $D^+$ and $D^-$ are present because of the symmetry in the bright field lighting technique (i.e. the light source 106 is located on the optic axis 110 of the CCD camera 108). The resulting poor image contrast and other shortcomings associated with the bright field illumination inspection system 100 are addressed by the present invention.

BRIEF DESCRIPTION OF THE INVENTION

The present invention includes an inspection system which uses an oblique illumination technique where the illumination symmetry is broken between the light source(s) and the CCD camera. This enhances the quality of the image. In addition, this type of inspection system enables one to indirectly extract the height of a glass surface discontinuity from the image. Thus, the need for using an additional glass surface discontinuity height sensor is eliminated.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
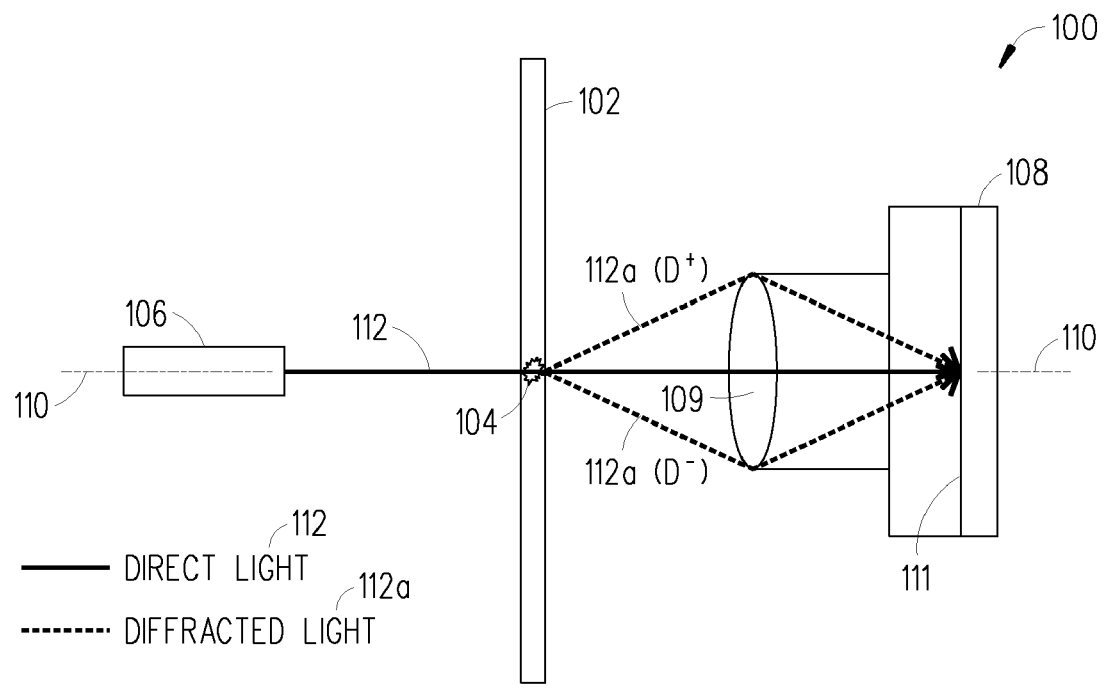
FIG. 1 (PRIOR ART) is a diagram illustrating the basic components of a traditional bright field illumination inspection system.

The present invention addresses the image contrast problem that is associated with the known bright field illumination inspection system 100 by breaking the symmetry of the lighting which occurs when the light source 106 is placed on the optic axis 110 of the CCD camera 108 (see FIG. 1). The symmetry may be broken by using an oblique illumination technique (anaxial illumination technique) in which one or more light sources is/are not placed on the optic axis of the CCD camera. Two exemplary oblique illumination inspection systems 200 and 300 are described next with respect to FIGS. 2 and 3.

Figure 2:
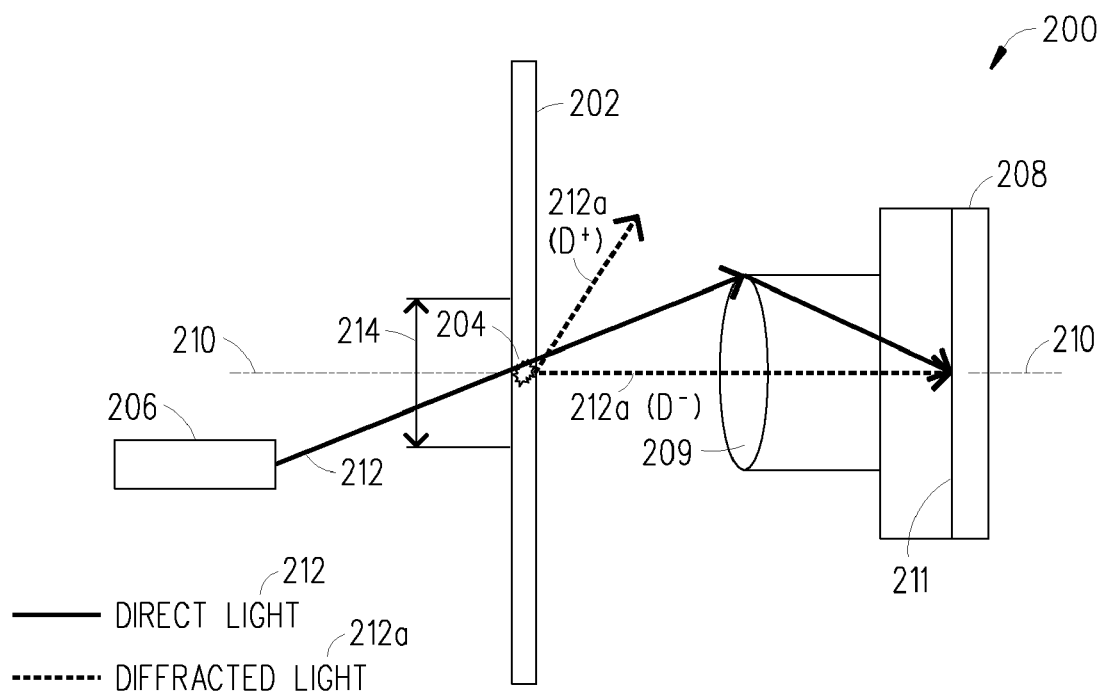
FIG. 2 is a diagram illustrating the basic components of an oblique illumination inspection system in accordance with a first embodiment of the present invention.

Referring to FIG. 2, there is shown an oblique illumination inspection system 200 that can be used to inspect a glass sheet 202 and identify defects 204 (one shown) on or within the glass sheet 202. The inspection system 200 includes a light source 206 (e.g., fiber line light source 206) and a CCD camera 208. The light source 206 and CCD camera 208 are located on opposite sides of the glass sheet 202, while the light source 206 is located off the optic axis 210 of the CCD camera 208 (this achieves the illumination symmetry breaking). In operation, the light source 206 emits a light beam 212 which passes through a portion of the glass sheet 202. The CCD camera 208 and in particular a camera lens 209 receives light 212 that passed un-deviated through the transparent defect 204. In addition, the CCD camera 208/camera lens 209 receives light 212a ($D^-$) that was diffracted by the transparent defect 204. However, the CCD camera 208/camera lens 209 do not receive light 212a (D+). The camera lens 209 focuses light 212 and 212a (D−) onto an image plane 211 within the CCD camera 208. The CCD camera 108 then creates a high contrast image which is used to detect, characterize and classify the defect 204 (see FIGS. 4 and 5).

Figure 5:
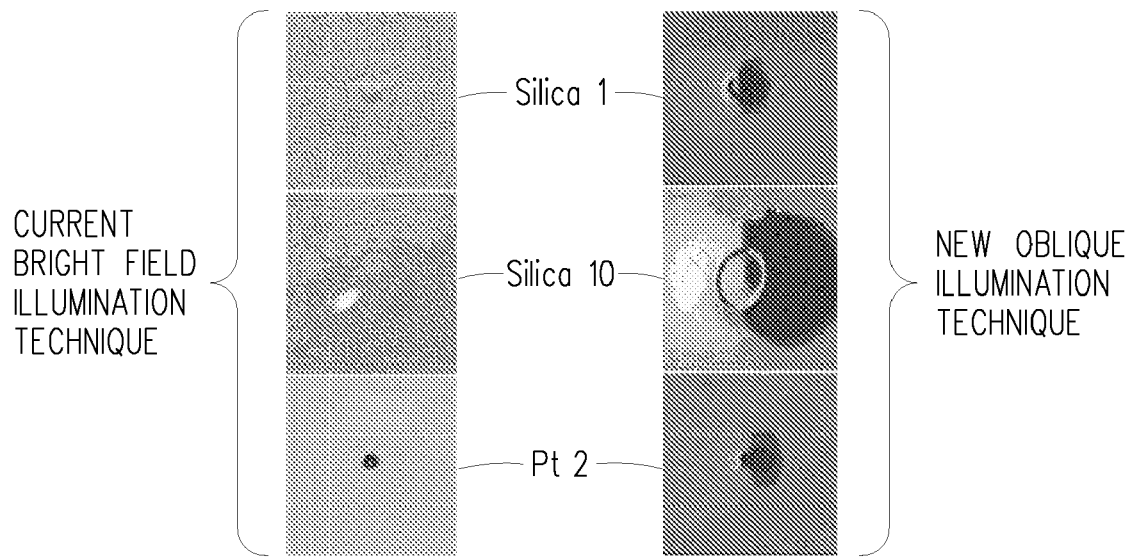
FIG. 5 has several images of defects obtained by using the traditional bright field illumination inspection system shown in FIG. 1 and several images of the same defects that where obtained by using the oblique illumination inspection system shown in FIG. 3 in accordance with the present invention.

The oblique illumination technique results in an image which has a much higher contrast of transparent glass defects, such as silica, scratches, and stains when compared to the known bright field illumination technique (see FIG. 5). As discussed above with respect to FIG. 1 (PRIOR ART), the symmetrical bright field illumination inspection system 100 generates an image that has a poor contrast because of the interference between the light 112 that passes un-deviated through the transparent defect 104 and the light 112a (D+) and 112a (D−) that was diffracted by the transparent defect 104. In particular, light 112a (D+) and 112a (D−) respectively have a positive diffraction order D+ and a negative diffraction order D− both of which interfere with the un-deviated light 112 to essentially wash out the contrast of the transparent defect 104 in the image.

This is not a problem with the oblique illumination technique, because the illumination symmetry is broken by offsetting the light source 206 from the optic axis 210 of the CCD camera 208. In particular, in the oblique illumination technique one of the complementary diffraction orders of the diffracted light 212a (D+) and 212a (D−) is suppressed and only the remaining diffraction order shown in this example as light 212a (D−) is allowed to interfere with the un-deviated light 212a. This results in an image being generated which has a contrast that is much higher than an image obtained by the symmetrical bright field illumination inspection system 100 (see FIG. 5).

Figure 3:
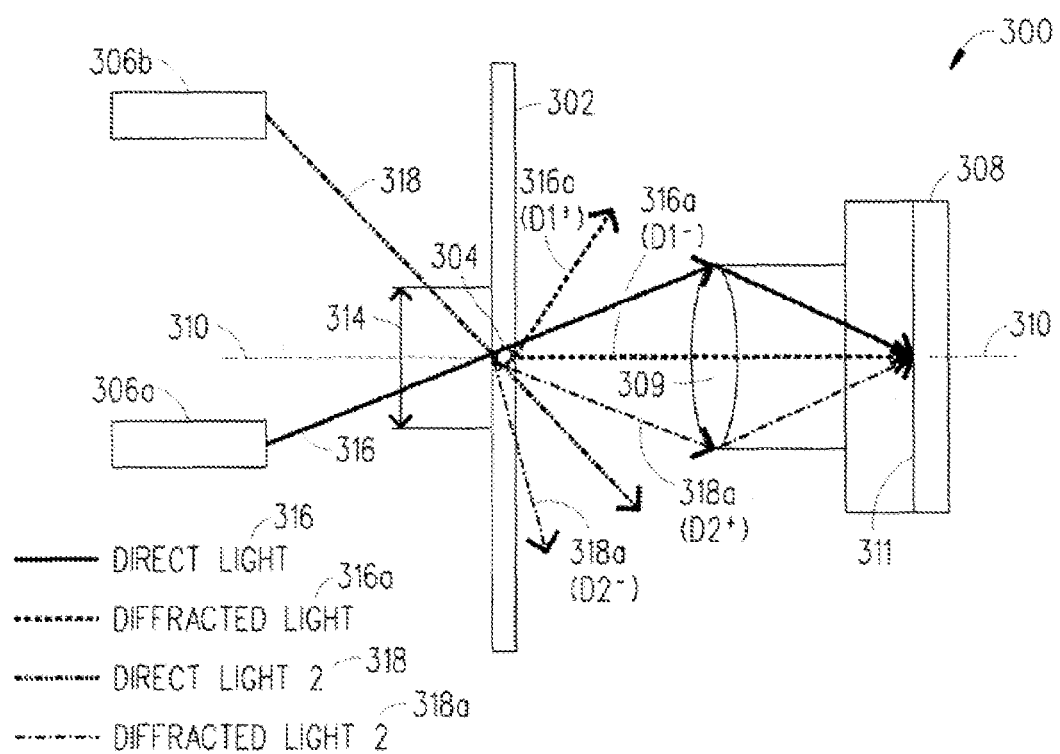
FIG. 3 is a diagram illustrating the basic components of an oblique illumination inspection system in accordance with a second embodiment of the present invention.

Referring to FIG. 3, there is shown another oblique illumination inspection system 300 that can be used to inspect a glass sheet 302 and identify defects 304 (one shown) on or within the glass sheet 302. The inspection system 300 includes a primary light source 306a (e.g., primary fiber line light source 306a), a secondary light source 306b (e.g., secondary fiber line light source 306b), and a CCD camera 308. The primary and secondary light sources 306a and 306b are located on one side of the glass sheet 302, while the CCD camera 308 is located on the opposite side of the glass sheet 302. As can be seen, both light sources 306a and 306b are offset from an optic axis 310 of the camera 308. The primary light source 306a is located closer to the optic axis 310 than the secondary light source 306b. As a result, the primary light source 306a provides a slow directional gradient illumination across a field of view 314 of the CCD camera 308 and is responsible for most of the image contrast enhancement. The secondary light source 306b provides a more balanced illumination across the field of view 314 in the CCD camera 308 and is responsible for image enhancement of the edges of the defect 304.

In operation, the light sources 306a and 306b respectively emit light beams 316 and 318 which pass through a portion of the glass sheet 302. The CCD camera 308 and in particular a camera lens 309 receives light 316 that passed un-deviated through the transparent defect 304. In addition, the CCD camera 308/camera lens 309 receives light 316a (D1−) that was diffracted by the transparent defect 204. Moreover, the CCD camera 308/camera lens 309 receives light 318a (D2+) that was diffracted by the transparent defect 204. However, the CCD camera 308/camera lens 309 does not receive light 316a (D1+), 318 and 318a (D2−). The camera lens 209 then focuses light 316, 316a (D1−) and 318a (D2+) onto an image plane 311 within the CCD camera 308. The CCD camera 108 then creates a high contrast image which is used to detect, characterize and classify the defect 304 (see FIGS. 4 and 5). If only one light source 206 is used as is the case with the oblique illumination inspection system 200, then there will be an intensity gradient across the field of view 214 in the CCD camera 208. This is necessary to develop the contrast enhancement effect. However, this gradient needs to be removed by software during the processing of the image. In contrast, if two light sources 306a and 306b are used as is the case with the oblique illumination inspection system 300, then this gradient is lessened to some degree such that software may not be needed to remove it during the processing of the image.

An advantage of the oblique illumination technique over the traditional bright field illumination technique is that the image contrast and resolution are enhanced. For instance, glass surface defects 204 and 304 such as scratches, stains, and onclusions which appear two dimensional under the standard bright field illumination technique now appear three dimensional under the oblique illumination technique of the present invention. This added dimensionality allows a human operator who is inspecting the glass sheet 202 and 302 to make a more accurate defect classification judgment. In turn, a more accurate defect classification judgment results in fewer glass sheets 202 and 302 being falsely rejected as defective. Thus, the quality of the inspection process is improved.

Figure 4:
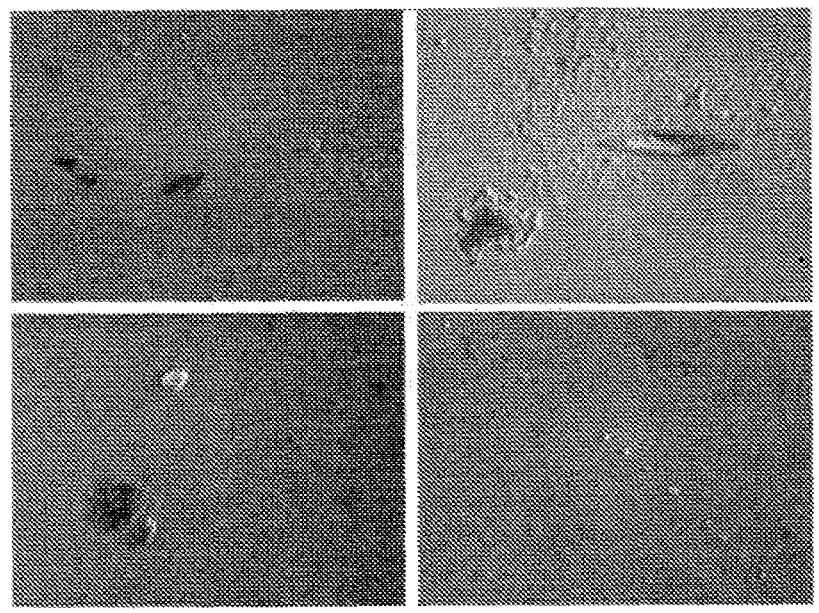
FIG. 4 illustrates several images of defects that where obtained by using the oblique illumination inspection system shown in FIG. 3 in accordance with the present invention.

Referring to FIG. 4, there are illustrated several images of surface defects which were obtained when testing the oblique illumination inspection system 300. As can be seen, the images clearly indicate the three dimensional nature of the various defects 304. These images have a much better quality than the images obtained by the known bright field illumination technique in which stains and particles would appear nearly invisible or opaque. A comparison of the differences between images obtained by the traditional bright field illumination inspection system 100 and images obtained by the oblique illumination inspection system 300 can be made by looking at the photos of FIG. 5. As can be seen, the silica/platinum defects are barely visible in the bright field images which were obtained by the traditional bright field illumination inspection system 100. While, the same silica/platinum defects are clearly visible in the gradient field images which were obtained by the oblique illumination inspection system 300.

Another advantage of the oblique illumination technique over the traditional bright field illumination technique is that the oblique illumination technique enables one to qualitatively measure the height of a surface discontinuity which is caused by a defect 204 and 304 embedded within the glass sheet 202 and 302. The height of the surface discontinuity can be indirectly calculated by analyzing the contrast variations (modulations) around the defect 204 and 304 in the surface defect image (see FIG. 5). In particular, the height of the surface discontinuity can be measured by: (1) determining the intensity of light on the left side of the defect 204 and 304 in the surface defect image; (2) determining the intensity of light on the right side of the defect 204 and 304 in the surface defect image; and (3) comparing the first intensity and the second intensity to determine a difference in intensities which is directly related to the height of the surface discontinuity.

The ability to qualitatively measure the height of a surface discontinuity using the present invention is a marked-improvement over the traditional bright field illumination inspection system 100, because, the bright field illumination inspection system 100 does not generate an image that enables one to qualitatively measure the height of a surface discontinuity. Instead, an additional off-line surface discontinuity height sensor would be needed to make this height measurement, which would slow down the defect inspection process. The oblique illumination inspection system 200 and 300 eliminates the need for using a separate surface discontinuity height sensor. This saves money and increases the speed at which the glass sheets 202 and 302 can be inspected.

Figure 6:
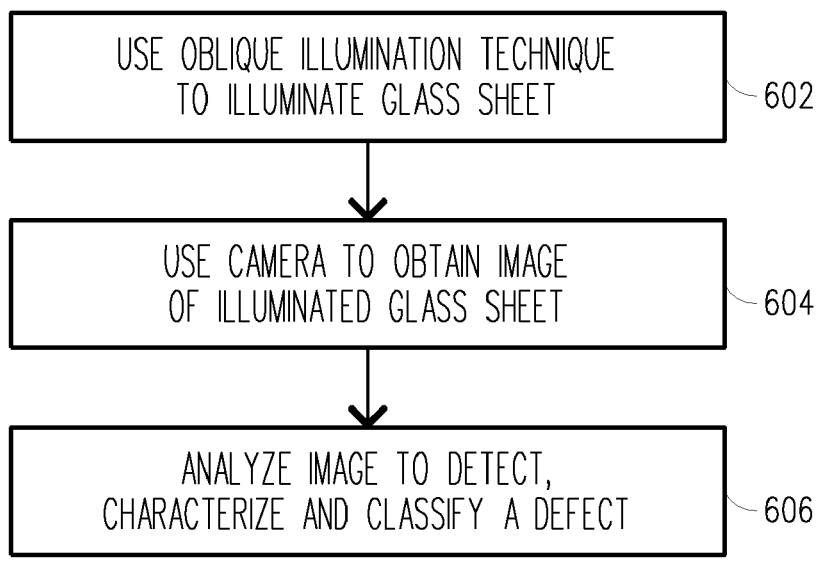
FIG. 6 is a flowchart illustrating the basic steps of a preferred method for inspecting a glass sheet in accordance with the present invention.

Referring to FIG. 6, there is a flowchart illustrating the basic steps of a preferred method 600 for inspecting a glass sheet 202 and 302 in accordance with the present invention. Beginning at step 602, the light sources 206, 306a and 306b (which form an oblique illumination system) are used to illuminate at least a portion of the glass sheet 202 and 302. At step 604, the CCD camera 208 and 308 is used to generate an image of at least a portion of the illuminated portion of the glass sheet 202 and 302. Then, the image is analyzed to detect, characterize and classify a defect 204 and 304 (if any) in the glass sheet 202 and 302. In the preferred embodiment, the image may be analyzed in a manner that removes camera noise (pixel variation, dust, etc.) and lighting gradients. In addition, the image may be analyzed to remove unwanted particles (e.g., based on size) and auto measure the size of the remaining defects 204 and 304.

Following are some additional features, advantages and uses of the oblique illumination technique of the present invention:

Manufacturers of glass sheets (glass substrates) which are incorporated into LCD display products would benefit from the use of the oblique illumination inspection system 200 and 300. Since, these glass sheets must be free from defects such as scratches, stains, and particle inclusions. The manufacturer could use the inspection system 200 and 300 to inspect the glass sheets while they are on the production finishing line before they are packed and shipped to a customer who assembles the LCD display products.

The inspection systems 200 and 300 described herein use an oblique transmission illumination technique to enhance image contrast over that of the traditional bright field illumination inspection systems. It should be noted that there are several other contrast enhancing techniques which can be used in addition to oblique illumination. Some of these techniques are as follows:

Coherent illumination.

Phase contrast illumination.

Differential interference contrast illumination.

Single sideband edge enhancement microscopy.

The inspection systems 200 and 300 can detect, characterize and classify many different types of defects 204 and 304 including an inclusion, an onclusion, a scratch, a stain, a blister, a cord, or a surface discontinuity (for example).

The glass sheets 202 and 302 described above can be made in accordance with a fusion process that is described in U.S. Pat. Nos. 3,338,696 and 3,682,60. The contents of these patents are incorporated herein by reference.

Although two embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An oblique illumination inspection system, comprising:
a primary light source that emits a first light beam which passes through a portion of a glass sheet;
a secondary light source that emits a second light beam which passes through the portion of the glass sheet;
a camera having an optic axis which is offset from said primary light source and said secondary light source that generates an image of the illuminated portion of the glass sheet where the image is used to detect, characterize and classify a defect of the glass sheet;
wherein said primary light source is responsible for image contrast enhancement of the defect because said primary light source provides a relatively balanced directional gradient illumination across the field of view of said camera which happens because the primary light source is located on one side of the optic axis of said camera and because the primary light source is located relatively close to the optic axis of said camera; and
wherein said secondary light source is responsible for image enhancement of edges of the defect because said secondary light source provides a relatively balanced directional gradient illumination across the field of view of said camera which happens because the secondary light source is located on another side of the optic axis of said camera and because the secondary light source is located relatively far from the optic axis of said camera.

2. The oblique illumination inspection system of claim 1, wherein if there is a defect in the glass sheet then said camera receives undeviated light and either a positive diffracted light or a negative diffracted light from said primary light source and said camera also receives either a positive diffracted light or a negative diffracted light from said secondary light source.

3. The oblique illumination inspection system of claim 1, wherein said defect is:
an inclusion;
an onclusion;
a scratch;
a stain;
a blister;
a cord; or
a surface discontinuity.

4. The oblique illumination inspection system of claim 1, wherein said image indicates the defect in three dimensions.

5. The oblique illumination inspection system of claim 1, wherein said image enables one to indirectly measure a height of a surface discontinuity which is caused if the defect is embedded within the glass sheet.

6. The oblique illumination inspection system of claim 5, wherein the height of the surface discontinuity is indirectly measured by:
determining a first intensity of light at a first side of the defect in the image;
determining a second intensity of light at a second side of the defect in the image; and
comparing the first intensity and the second intensity to determine a difference in intensities which is directly related to the height of the surface discontinuity.

7. A method for inspecting a glass sheet, said method comprising the steps of:

using an oblique illumination system to illuminate and obtain an image of at least a portion of a glass sheet which has a defect, where said using step further includes:
  using a primary light source to emit a first light beam which passes through a portion of a glass sheet;
  using a secondary light source to emit a second light beam which passes through the portion of the glass sheet;
  using a camera having an optic axis which is offset from the primary light source and the secondary light source to generate the image of at least a portion of the illuminated portion of the glass sheet;
  wherein said primary light source is responsible for image contrast enhancement of the defect because said primary light source provides a relatively balanced directional gradient illumination across the field of view of said camera which happens because the primary light source is located on one side of the optic axis of said camera and because the primary light source is located relatively close to the optic axis of said camera; and
  wherein said secondary light source is responsible for image enhancement of edges of the defect because said secondary light source provides a relatively balanced directional gradient illumination across the field of view of said camera which happens because the secondary light source is located on another side of the optic axis of said camera and because the secondary light source is located relatively far from the optic axis of said camera;
analyzing said image to detect, characterize and classify the defect of the glass sheet; and
outputting the results of the analyzing step.

8. The method of claim 7, wherein said defect is:
an inclusion;
an onclusion;
a scratch;
a stain;
a blister;
a cord; or
a surface discontinuity.

9. The method of claim 7, wherein said image indicates the defect in three dimensions.

10. The method of claim 7, further comprising the step of analyzing said image to indirectly measure a height of a surface discontinuity which is caused if the defect is embedded within the glass sheet, wherein said analyzing step further includes:
  determining a first intensity of light at a first side of the defect in the image;
  determining a second intensity of light at a second side of the defect in the image; and
  comparing the first intensity and the second intensity to determine a difference in intensities which is directly related to the height of the surface discontinuity.

* * * * *